US010301167B2

(12) United States Patent
Johnson et al.

(10) Patent No.: US 10,301,167 B2
(45) Date of Patent: May 28, 2019

(54) APPARATUS AND METHOD FOR AUTOMATICALLY UPDATING THE RELATIONSHIP BETWEEN MEASURED STORAGE TANK DEPTH AND STORAGE TANK VOLUME, AND MONITORING THE ACCURACY OF A DISPENSER FLOW METER

(71) Applicants: Paul Johnson, Tallahassee, FL (US); Thomas D'Alesandro, Ronkonkoma, NY (US); Mark Butsch, Tallahassee, FL (US)

(72) Inventors: Paul Johnson, Tallahassee, FL (US); Thomas D'Alesandro, Ronkonkoma, NY (US); Mark Butsch, Tallahassee, FL (US)

( * ) Notice: Subject to any disclaimer, the term of this patent is extended or adjusted under 35 U.S.C. 154(b) by 93 days.

(21) Appl. No.: 15/226,968

(22) Filed: Aug. 3, 2016

(65) Prior Publication Data
US 2018/0037451 A1 Feb. 8, 2018

(51) Int. Cl.
*B67D 7/08* (2010.01)
*B67D 7/78* (2010.01)
*G01F 1/86* (2006.01)
*G01F 22/00* (2006.01)
*G01F 25/00* (2006.01)
*G01N 9/00* (2006.01)
*G01F 1/00* (2006.01)

(52) U.S. Cl.
CPC ............... *B67D 7/085* (2013.01); *B67D 7/78* (2013.01); *G01F 1/007* (2013.01); *G01F 22/00* (2013.01); *G01F 25/0007* (2013.01); *G01N 9/00* (2013.01); *G01F 25/0038* (2013.01)

(58) Field of Classification Search
CPC .. B67D 7/085; B67D 7/14; B67D 7/78; G01F 1/86; G01F 23/00; G01F 25/0007; G01N 9/00
See application file for complete search history.

(56) References Cited

U.S. PATENT DOCUMENTS

| | | | | |
|---|---|---|---|---|
| 5,363,093 A * | 11/1994 | Williams | ................ | B67D 7/08 340/605 |
| 5,665,895 A * | 9/1997 | Hart | ....................... | G01F 1/007 702/100 |
| 6,691,061 B1 * | 2/2004 | Rogers | ............... | G01F 23/0069 702/156 |
| 2006/0157150 A1 * | 7/2006 | Blakeslee | ............... | B67D 7/08 141/198 |

* cited by examiner

Primary Examiner — Manuel L Barbee
(74) Attorney, Agent, or Firm — J. Wiley Horton

(57) ABSTRACT

An automated liquid inventory monitoring and inventory reconciliation system. The system uses a liquid densitometer to precisely measure the density of liquid being dispensed. This allows the system to account for the significant temperature-induced volume variations existing in common liquids such as gasoline. In the preferred embodiments, a fuel inventory processor tracks the quantity of fuel loaded into the tank and the quantity of fuel dispensed to maintain an ongoing computation of the quantity of fuel that should be present in the tank. An accurate tank depth measurement device is also employed. The processor compares the tank depth measurement to the computed quantity of fuel in the tank and uses the values to create an updated tank strapping chart.

13 Claims, 13 Drawing Sheets

APPARATUS AND METHOD FOR AUTOMATICALLY UPDATING THE RELATIONSHIP BETWEEN MEASURED STORAGE TANK DEPTH AND STORAGE TANK VOLUME, AND MONITORING THE ACCURACY OF A DISPENSER FLOW METER

CROSS-REFERENCES TO RELATED APPLICATIONS

Not Applicable

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of liquid dispensing measurement and control. More specifically, the invention comprises a system and method for accurately correlating liquid level measurements within a storage tank to the volume or mass of liquid contained within the tank. Among other things, the inventive system may be used to confirm the accuracy of a dispenser flow meter.

2. Description of the Related Art

Many different types of liquids are stored and later dispensed. Most dispensed liquids are purchased on the basis of a price per unit volume. One common example is the dispensing of liquid fuels such as gasoline or diesel fuel. Gasoline will be used as an example in the following descriptions of the prior art, but the reader should bear in mind that the prior art encompasses many different liquids and the inventive concepts described in this disclosure likewise encompass many different liquids.

Gasoline is stored in tanks. These are often underground tanks but many tanks are above ground. In fact, the recent trend is toward above-ground tanks. The fuel dispensed from any type of storage tank is generally passed through some type of flow meter to accurately determine the volume of fuel actually transferred to the tank of a vehicle. In addition, it is important for the fuel vender to accurately monitor the level of liquid within the underground storage tank. This permits the vendor to monitor the inventory and forecast the need for replenishment.

The amount of fuel within an underground tank is most often monitored using a linear depth meter. The depth meter can be quite accurate. However, the correlation of measured depth to tank volume is often not very accurate. The tanks are accurately measured when they are newly fabricated and free-standing. A depth-to-volume correlation chart is then created for each individual tank. This process is traditionally called "strapping the tank." "Strapping" refers to the process of using marked steel straps to precisely measure the circumference of the tank at fixed intervals along its length (fir a horizontally-oriented tank) or along its height (for a vertically-oriented tank). The circumference measurements are used to build a depth-versus-volume chart for a particular tank. This correlation chart is often referred to as a "strapping chart."

Strapping charts may also be made by adding precisely-measured liquid volumes to a tank and recording the resulting depth on a linear tank gauge. This approach accommodates complex tank geometry (such as a ribbed wall) and manufacturing tolerances. It can produce an accurate strapping chart—at least for the geometry that exists at the time of manufacturing and before the tank is installed.

One may in theory develop an equation for converting linear depth measurements into corresponding volumes, but this is quite complex for even a basic tank design. A simple example serves to illustrate this point. Consider a cylindrical tank with the central axis of the tank lying horizontally. The tank has a radius r and a length l. The ends of the tank are assumed to be perfectly flat plates (unrealistic but this assumption greatly simplifies the calculation). The wall of the tank is assumed to be a perfect cylinder (also unrealistic). A coordinate system is created with the origin lying on the cylinder's central axis. The vertical position of the surface of the fuel within the tank is denoted as y. Thus, y varies from $-r$ to $+r$. The equation for the volume v may then be written as:

$$v = r^2 l \sqrt{1-y^2} y + \cos^{-1}(-y)$$

The same equation may be derived from geometry or by using calculus. Either way, the reader will note that the relationship between the depth y and the volume v is rather complex, despite the simplifying assumptions made in this example. If one assumes semi-hemispherical or hemispherical end caps, the relationship becomes much more complex. Further, the assumption of a cylindrical wall is unrealistic. Tanks are theoretically cylindrical but the manufacturing tolerances are significant. For these reasons an equation relating the depth measurement to the volume is not commonly used in industry. Instead, the empirically-derived "strapping chart" is used. Even this approach has problems, however.

When a tank is installed its geometry is invariable altered. An above-ground tank distorts as fuel weight is added. It is often also distorted by differential heating (The side of the tank facing the sun may be much hotter than the other side). A buried tank may see even greater distortion. When a tank is buried in the ground, the soil under it settles and the addition of the substantial fuel weight causes the tank to deform in unpredictable ways. An error in the strapping chart is thereby introduced. If left uncorrected, this error will persist for the entire useful life of the tank.

In addition, the amount of tank deformation is often not static. Soil subsidence may increase over time. The moisture content of the soil will also change over time. The result is that one cannot say with certainty that soil subsidence will increase to a point and then stabilize. In some installations the tank deformation may even be cyclic.

FIG. 1 provides a simplified elevation view of a buried gasoline storage tank connected to a dispenser. Tank 10 is buried beneath concrete slab 18. The tank is typically surrounded by a stabilizing media 20—often a mixture of gravel and smaller particles. Fuel 12 occupies the bottom of the tank up to surface 38. Ullage 40 lies above surface 38 ("ullage" being an old English term for the amount by which a container falls short of being full).

Several access ports are typically provided through slab 18 to tank 10. Fill access 14 provides external access to fill pipe 16. The fill pipe is used to transfer fuel from a tanker truck into the underground tank. In this example it is simply a vertical pipe with an access cover at its upper end. The bottom end is open so that fuel pumped into the top of the pipe flows down and into the tank.

The access near the middle of the tank provides an entry point for an automatic tank gauge (ATG probe 24). This device is used to determine the current linear position of surface 38. Probe head 26 is mounted to the top of ATG probe 24. Automatic tank gauge controller 22 communicates with probe head 26 (This may be a wired or wireless connection). The automatic tank gauge controller is usually remotely located—such as in a nearby building. The controller monitors and records the liquid level. More sophisticated examples include an associated memory device that stores the strapping chart for the specific tank and a processor that converts the measured liquid level into a "gallons remaining" readout. Very sophisticated examples may even monitor the volume of fuel dispensed and compare this to the calculated value for the volume remaining in the tank. This feature is sometimes referred to as an "inventory reconciliation."

FIG. 12 shows an elevation view of a sophisticated automatic tank gauge. This version includes the ability to separately monitor the position of two independent floats—fuel level float 120 and water level float 122. Fuel level float 120 is configured to float on surface 38 of the fuel contained within the tank. Water level float 122 is configured to measure the depth of any water contained in the bottom of the tank. The density of the water level float is configured so that it sinks through the fuel but floats on the water (owing to the fact that the density of hydrocarbon fuels is less than the density of water). Water level float 122 floats on fuel water/interface 126. ATG probe 24 precisely reports on the depth of surface 38 and on the depth of fuel/water interface 126 (assuming that water is found in the bottom of the tank).

In addition, this particular ATG probe 24 includes five separate temperature sensors 124. These provide temperature information to automatic tank gauge controller 22 (see FIG. 1) which may then be used in different ways. The controller "knows" the depth of fuel in the tank. It therefore "knows" which temperature sensors are wetted by fuel and which are not. It may use the temperature readings from the wetted sensors to determine an average temperature for the fuel in the tank.

The access port shown to the left in FIG. 1 provides access for intake line 30. This intake line is connected to pump 28. The pump draws fuel out of tank 10, pressurizes it, and sends it out through discharge line 32. Vent 34 vents any accumulated fuel vapors to the atmosphere or into a collection system. The discharge line leads to dispenser 36.

Dispenser 36 is a dispensing station familiar to those skilled in the art. Modern versions typically include the ability to dispense three or more different fuels (such as "regular," "mid-grade," "premium," and possibly diesel). It includes dispenser nozzles configured to fit into a vehicle's filler neck. It also includes payment-receiving devices such as a credit card reader. Display devices are also included to display selections made, price charged, and volume dispensed.

Multiple discharge lines 32 typically feed into a single dispenser 36. For example, a dispenser that is able to dispense three different types of fuel may have three different discharge lines leading in. Most dispensing stations have multiple dispensers. However, most stations also only have a single underground tank for each type of fuel sold. As an example, a station selling three different grades of gasoline would have three different storage tanks but might have six or more dispensers. In that case discharge line 32 would be split so that is can feed all six available dispensers. The single pump 28 pressurizes the distribution network for a particular fuel type to all the dispensers. Each dispenser contains a metering device for measuring the volume of fuel dispensed but typically does not contain a separate pump. Those skilled in the art will know that "mid-grade" fuels are often created on-site by blending regular and premium grades, but even these facilities would have at least two tanks and two lines leading to each dispenser.

FIG. 7 depicts some of the internal components of dispenser 36. The particular dispenser shown dispenses three different grades of gasoline (low-grade, mid-grade, and premium). Three discharge lines (32L, 32M, and 32H) arrive at the dispenser from three different underground tanks. Each discharge line typically includes a valve 82 regulating flow of the particular fuel into the dispenser. Downstream of each valve 82 is a piston flow meter 62. A piston flow meter is a precise device that rotates a fixed amount for each volume of fuel passing through it. In older designs the piston flow meter would drive a volume and price display through a set of gears. In modern dispensers the rotation of each piston flow meter is monitored by a rotary encoder 80. This device creates a train of electronic pulses that is counted and analyzed by a separate processor. The processor translates the pulses into the volume and price display (now typically a graphical display such as a color LCD).

A nozzle feed line 88 leads out of each piston flow meter and ultimately leads to the dispensing nozzle itself. As those skilled in the art will know, a separate flow control valve exists on the nozzle. Check valves are used to prevent cross-contamination among the different fuels.

FIG. 6 shows a single piston flow meter 62 in greater detail. Those knowledgeable in the field of fuel dispensing will recognize this device as a standard one that has been used for many years. Its use is required by many regulatory agencies and—while it is an old design—its continued use is expected.

Input pipe 68 allows fuel to enter the pump and output pipe 70 carries the same fuel out of the pump. Housing 64 includes four perpendicular cylinders—each of which is covered by a cylinder cover 66. Each cylinder includes a linearly translating metering piston. Flow through the pump causes the metering pistons to move back and forth over their range of travel. The motion of the metering pistons rotates the meter output shaft 78. The result is that each rotation of meter output shaft 78 corresponds to a precisely-known volume of fuel passing through the pump.

Rotary encoder 80 is coupled to meter output shaft 78. As described previously, the rotary encoder typically provides a pulsed output that allows a separate processor to monitor the rotation of the output shaft and thereby infer the volume of fuel dispensed.

Piston flow meters usually have a calibration wheel 72. Rotating the calibration wheel alters the volume of fuel dispensed per revolution of meter output shaft 78. The calibration wheel is often set by a "weights and measures" governmental regulatory agency. Once it is set lock pin 74 is inserted and a tamper-proof calibration seal 76 is put in place. These devices prevent any unknown movement of the calibration wheel.

Of course, all machines containing moving parts wear over time. The cylinder bores grow larger with wear and internal leakage past the pistons may increase with time. For these reasons and others a piston flow meter does not remain calibrated forever. Its output will drift over time. This "meter drift" phenomenon has long been known. It is the reason that piston flow meters must be periodically recalibrated. New measurements are made during the recalibration process and the calibration wheel is moved to a new position and locked in place.

The calibration process is manual and it can be time consuming. A fixed calibration container (often called a "prover") is filled with fuel while the measured volume from the flow meter is observed. The flow meter is then adjusted to ensure that the volume it measures matches the volume dispensed into the prover. This process may require more than one fill cycle of the prover.

State statutes often impose fines for any miscalibration that "shorts" the consumer. If such a miscalibration is deemed deliberate, the operator can be fined up to 10,000 U.S. dollars per day. There is generally no fine for a miscalibration in favor of the consumer. However, an error in favor of the consumer effectively gives away free fuel and no operator can afford to do that for long. Thus, there is a strong incentive to keep the flow meters in calibration.

Recalibration intervals are somewhat arbitrary. For some piston flow meters the specified interval is too long and for others it is too short. In the prior art it is not possible to accurately measure the drift of a piston flow meter. Thus, it is not possible to directly know whether the meter remains within a specified tolerance. The setting of a somewhat-arbitrary recalibration interval is intended to ensure that the vast majority of piston flow meters in use will remain in calibration. As one would expect, the way to ensure this is to use a conservative recalibration interval. The result is that many meters will be recalibrated when there was no need to recalibrate. Since recalibration is rather expensive, both in terms of labor and down-time, the current system is inefficient.

The volume and temperature of fuel delivered into an underground tank is accurately known. If one could accurately measure the volume and temperature of fuel in the tank over time, one could then infer the volume dispensed and compare this value with the value measured by the piston flow meter. This comparison would then show whether the piston flow meter accuracy had "drifted" outside the allowable tolerance. Unfortunately, determining the volume of fuel contained within a tank is not an easy problem.

As explained previously, this is most often done using a "tank strapping" chart. FIGS. 2 through 5 illustrate some of the problems experienced when applying a "tank strapping" chart to convert a measured linear depth to a volume of fuel remaining. Systems for converting a measured depth to a remaining volume are fairly complex. FIG. 2 illustrates the cross section of a perfect cylinder having perfectly flat end plates. In FIG. 2(A) the tank is nearly empty. In FIG. 2(B) the tank is about 50% full. From even a casual visual inspection the reader will observe that the same change in measured depth ("Δh") equates to a very different change in volume for the two examples. The depth change in FIG. 2(B) represents a much wider "slice" of the tank.

Many tanks employ semi-hemispherical end caps and a ribbed main section. The geometry involved in these cases is much more complex, even when the tank is first completed and not yet buried in the ground. When the tank is buried and loaded with fuel a more complex shape results. FIG. 3 depicts a cross section through a buried tank. Circular section 42 represents the ideal, undeformed and circular cross section. Slumped section 44 represents the shape that actually results from the installation process. The degree of slump and the shape of the slump is largely unpredictable.

FIG. 4A depicts the fact that most tank installations are not perfectly level. Some slope angle ("α") will be present. In fact, some slope is often deliberately introduced so that the tank will have a known low point. The slope angle is exaggerated in FIG. 4 for purposes of visualization. However, even a small slope angle means that surface 38 will not be parallel to the tank's central axis. This fact makes the correlation of depth to volume still more complex.

FIG. 4B depicts the fact that most tank installations also contain some amount of roll angle ("β"). The roll angle may cause the automatic tank gauge probe to be non-perpendicular to the surface of the fuel in the tank. An additional error is thereby introduced.

Finally, FIG. 5 depicts the effects of uneven subsidence during installation. The right end of the tank (with respect to the orientation in the view) has subsided more than the left end. The tank no longer has a linear centerline. Instead, the centerline may be more of a spline.

Other distortion phenomena exist in some installations. Even if one can accurately determine an equation or empirical table for correlating depth to volume as a tank is manufactured, the correlation will not tend to remain accurate after installation. Further, the correlation will tend to change over time.

There are now laser-based systems that actually allow a strapping chart to be created in situ by lowering a measurement system into the tank. Even these are prone to error, however, since the full tank will move with respect to the empty tank and the tank geometry will tend to change over time due to soil subsidence, etc.

Despite these issues there is no doubt that an accurate linear depth measurement can be obtained for the tank when it is completely full. If one can precisely measure the quantity of fuel dispensed over time then it seems at least theoretically possible to create an in situ strapping chart by starting with a full tank and measuring the amount dispensed and the linear depth as the tank goes down. There is another significant problem with this approach, however.

A piston flow meter as shown in FIG. 6 measures the volume of fuel dispensed. Assuming an underground tank is not leaking (and not venting), the mass of fuel contained within the tank remains constant. However, because the density of most fuels is temperature-dependent, the volume of fuel (as opposed to the mass) changes over time.

The density of gasoline, for example, is much more temperature dependent than that of water. At 20° C., the rate of change in the density of gasoline with respect to temperature is about 4.5 times that of water. This strong temperature dependence has long been a recognized problem in fuel dispensing and a table of correction factors is used to compensate for it. Wholesale gasoline sales use these correction factors to ensure that the wholesale purchaser pays for the delivered volume corrected to a standard temperature.

Within the fuel dispensing industry, a standard temperature of 15° C. or 60° F. is used (even though these two values are not precise equivalents since 15° C. is actually 59° F.). A table of correction factors is used to correct for non-standard temperature. The term "gross sale" refers to a volume sold at the actual dispensing temperature, uncorrected from any deviation from the defined standard temperature. The term "net sale" refers to a volume corrected for non-standard temperature. Thus, on a hot day a gross sale transfers relatively less mass and on a cold day a gross sale transfers relatively more mass. A net sale, on the other hand, is supposed to transfer the same mass no matter what the ambient temperature is.

When fuel is transferred from a tanker truck into an underground storage tank this is considered a "wholesale" transaction and temperature correction is routinely applied. The overarching concept of temperature correction is to price the transaction at a unit price per unit volume—where the unit volume is the volume that would have been measured if the temperature had been dead on the standard temperature of 15° C. Another way to state this is that the price paid is effectively a price per unit mass transferred and the correction factors are used to convert measured volume into actual mass. The reader should bear in mind, however, that the industry does not generally speak of these transactions as mass transfers.

Some examples serve best to illustrate these concepts: In all cases the transfer is measured as a volume of fuel. If the temperature of the fuel being transferred is 15° C. then no correction is required. In the standard table the "correction factor" for this condition is simply 1.0000. Thus, if 1,000 U.S. gallons are transferred at a wholesale rate of 2.00 U.S. dollars per gallon and a temperature of 15° C. (approximately 60° F.), then the payment will be 2,000 U.S. dollars.

Consider next what happens if the fuel being transferred has a temperature of 25° C. (approximately 77°). According to the American Petroleum Institute ("API"), the volume correction factor at 25° C. is 0.9874 (Note that there is no correction for variations in atmospheric pressure as its effect is negligible). A temperature of 25° C. is 100 above standard and the correction factor should be applied. The volume for the transaction is adjusted as 1,000 U.S. gallons multiplied by 0.9874 for a net result of 987.4 temperature-compensated gallons purchased. The payment will then be 2.00 multiplied by 987.4, or 1,974.80 U.S. dollars.

In the United States, however, retail fuel purchases have not traditionally been subject to temperature compensation. Returning to FIG. 7, the reader will note that the retail dispenser 36 only contains volumetric flow measuring devices (piston flow meters 62). Thus, the temperature of the fuel being dispensed is not normally measured. While the fuel inventory control system might accurately "know" the volume of fuel being dispensed, it is difficult to correlate this amount to tank volume because of the fuel's unknown density variation.

Storage tanks are buried to an average depth of about 2 meters and surrounding soil temperatures at that depth remain fairly constant—though they do increase and decrease with the changing seasons. If gasoline remained in an underground tank stored for a long time it would likely reach a stable temperature that is comparable to the temperature of the surrounding soil. One could then use this as a standard temperature and accurately translate the measured dispensed volume into tank depth measurements.

But, even a medium-sized station will sell 10,000-15,000 gallons of fuel per day and this means that a tanker truck visits the station about once per day (and multiple times for larger stations). Most of the volume within any given tank turns over in 24 hours. Most modern underground storage tanks are made of non-metallic materials such as fiberglass. These tanks tend to be good thermal insulators. Thus, the fuel placed in an underground tank will not change temperature very rapidly. It may take a day or more to reach the temperature of its surroundings.

Fuel loaded into the tanker truck tends to be stored above ground and the tanker truck itself is of course above ground. Further, the tanker truck uses a thermally conductive tank that is exposed to rapidly moving ambient air. The result is that the fuel within a tanker tends to have a temperature that is close to the average ambient air temperature. In Minnesota in January this would be −11° C. In Florida in July this would be 30° C.

The temperature of the surrounding soil tends to be site-specific. In Minnesota in January the soil temperature at a 2 meter depth averages about 7° C. (45° F.). In Florida in July the deep soil temperature averages about 26° C. (78° F.). The fuel delivered from the winter tanker in Minnesota must increase in temperature over a spread of 18° C. The fuel delivered from the summer tanker in Florida must decrease in temperature over a spread of 4° C.

In either case the temperature variation complicates the reconciliation of fuel volume remaining in the tank against the volume of fuel that has been dispensed. In the case of the winter-time Minnesota tanker, if 1,000 gallons of cold gasoline are loaded into an underground tank and allowed to rest until reaching the ambient deep soil temperature, the 1,000 gallons will expand to be 1,042.5 gallons. In other words, one could dispense 42.5 gallons from the tank but the linear depth gauge in the tank would still show the tank to be absolutely full.

In the case of the summer-time Florida tanker, if 1,000 gallons of hot gasoline are loaded into an underground tank and allowed to rest until reaching the ambient temperature, the 1,000 gallons will contract to be 994.8 gallons. Even with no dispensing, 5.2 gallons will seem to "disappear."

In recent years very accurate liquid densitometers have become available. These devices are able to accurately measure the density of a liquid as it is dispensed. Very accurate tank depth gauges are also available. A new system that takes advantage of the capabilities of these sensing devices is desirable. In particular, a system that is able to accurately reconcile measurements of dispensed fuel against measurement of fuel retained in the tank is desired. The present invention provides just such a system.

BRIEF SUMMARY OF THE PRESENT INVENTION

The present invention comprises an automated fuel inventory monitoring and inventory reconciliation system. The system uses a liquid densitometer to precisely measure the density of fuel being dispensed. This allows the system to account for the significant temperature-induced volume variations existing in common fuel such as gasoline. In the preferred embodiments, a fuel inventory processor tracks the quantity of fuel loaded into the tank and the quantity of fuel dispensed to maintain an ongoing computation of the quantity of fuel that should be present in the tank.

An accurate tank depth measurement device is also employed. The processor compares the tank depth measurement to the computed quantity of fuel in the tank and uses the values to create an updated tank strapping chart. The tank strapping chart is preferably updated regularly over time so that variations in tank geometry caused by subsidence etc. can be corrected. The processor can also use the updated tank quantity calculations to monitor the accuracy of a piston flow meter that is present for regulatory purposes.

Figure 1:
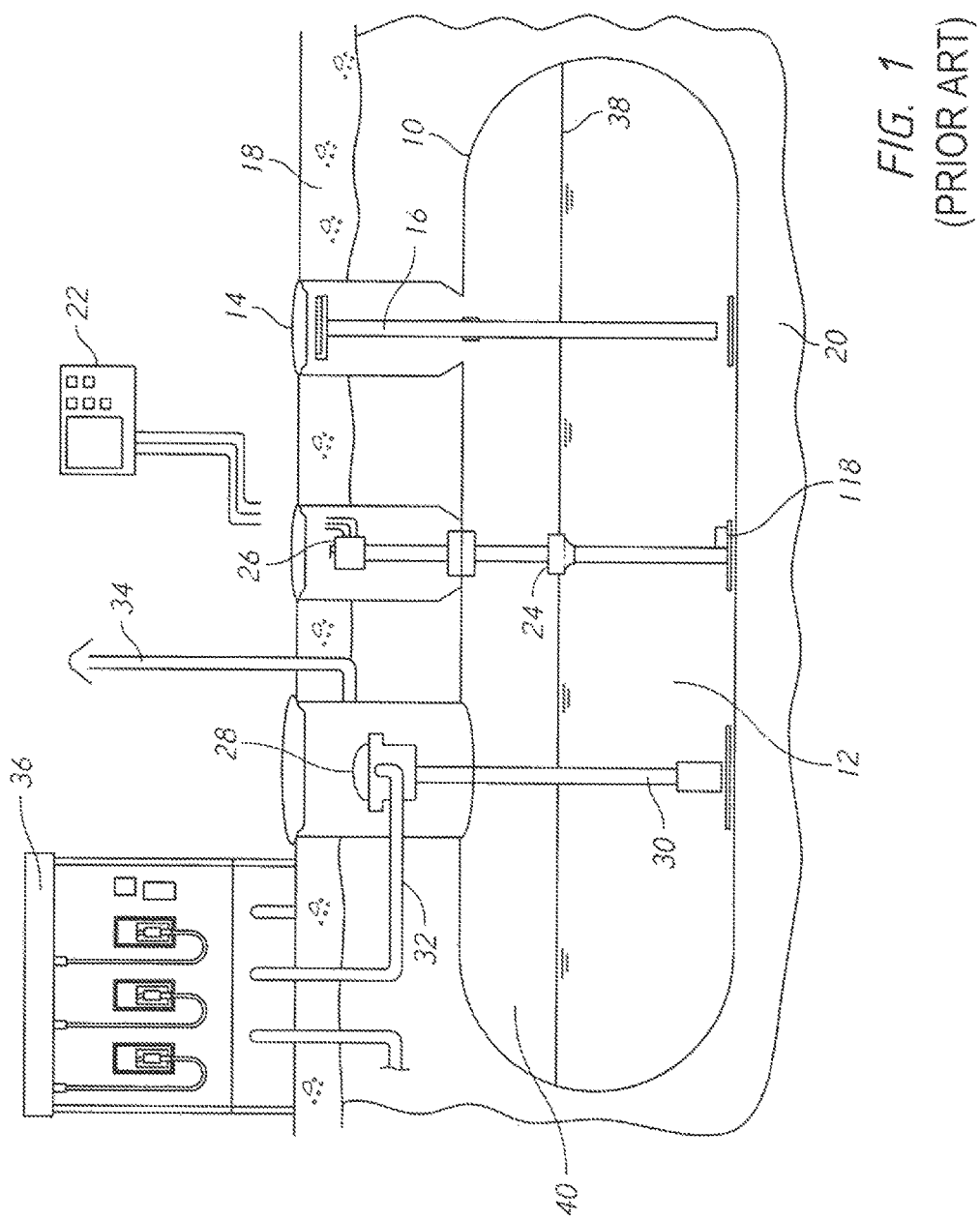
FIG. 1 is a simplified elevation view, showing a prior art underground fuel storage tank and associated components.
Figure 2A:
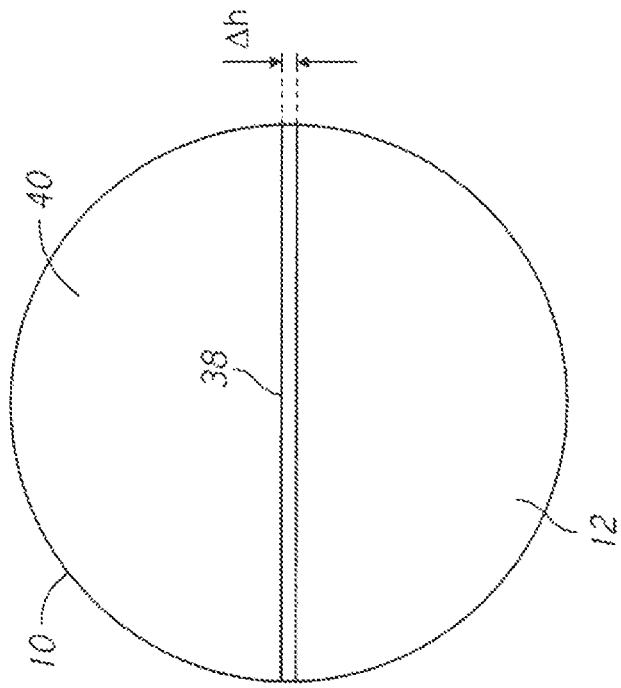
FIG. 2A is a sectional elevation view, showing an underground fuel storage tank with different fuel volumes.
Figure 2B:
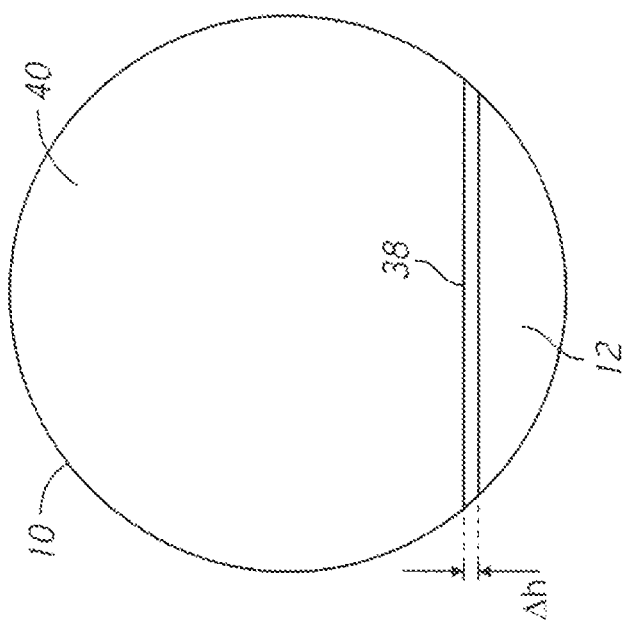
FIG. 2B is a sectional elevation view, showing an underground fuel storage tank with different fuel volumes.
Figure 3:
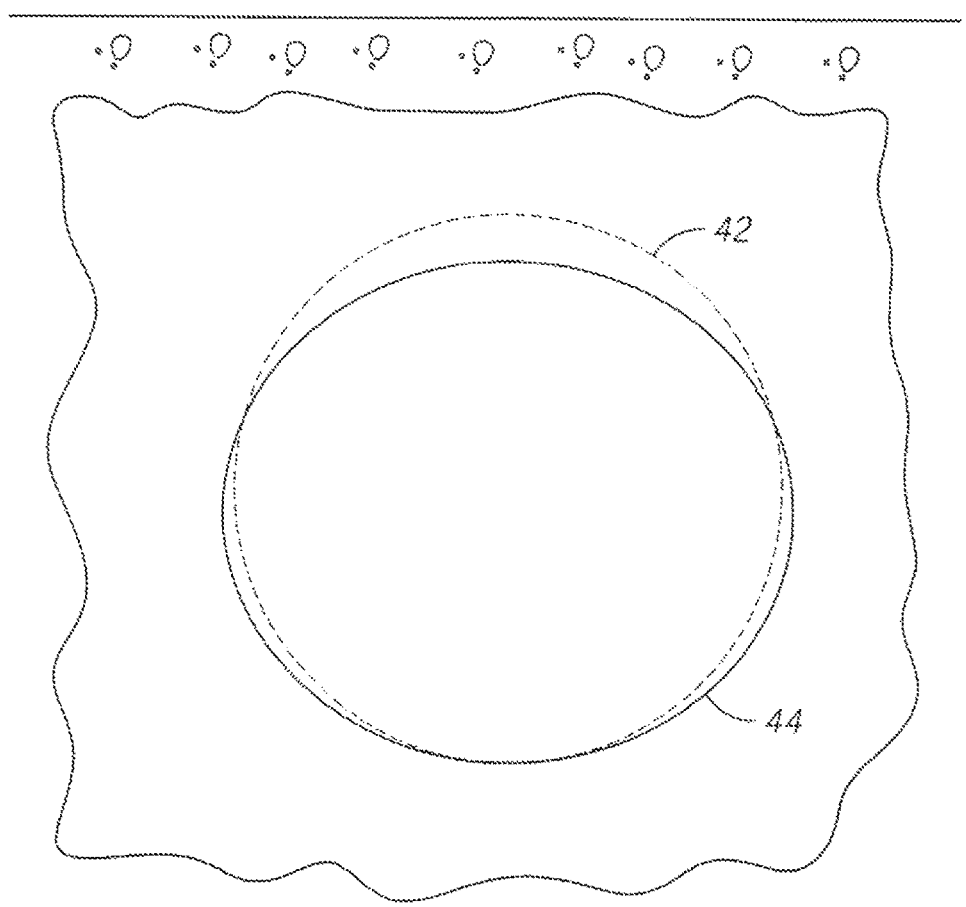
FIG. 3 is a sectional elevation view, showing the effect of slump on the circular cross-section of a storage tank.
Figure 4A:
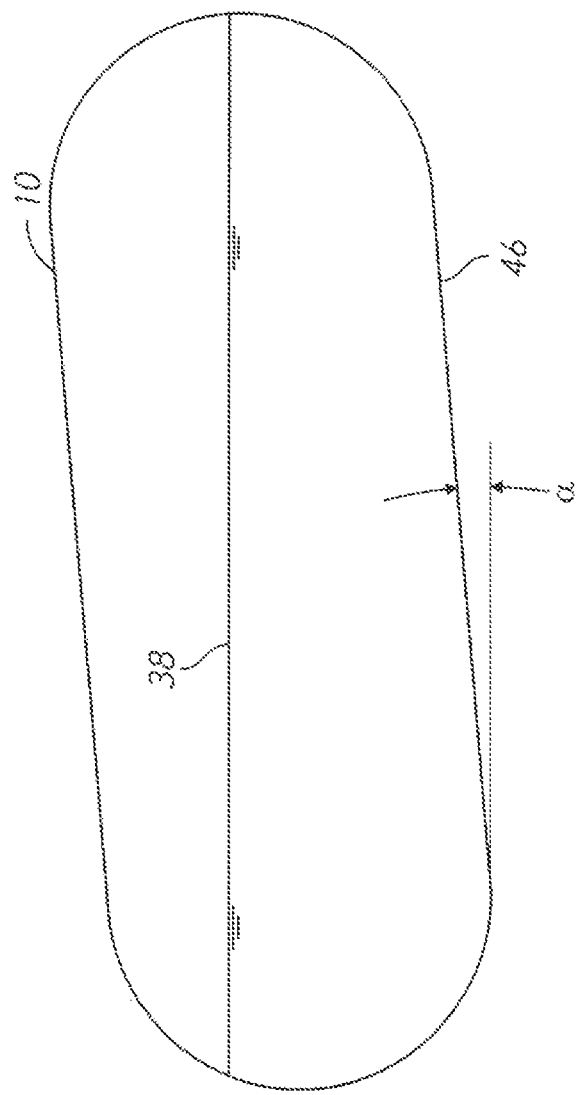
FIG. 4A is a sectional elevation view, showing the effect of slope (pitch) on an underground storage tank.
Figure 4B:
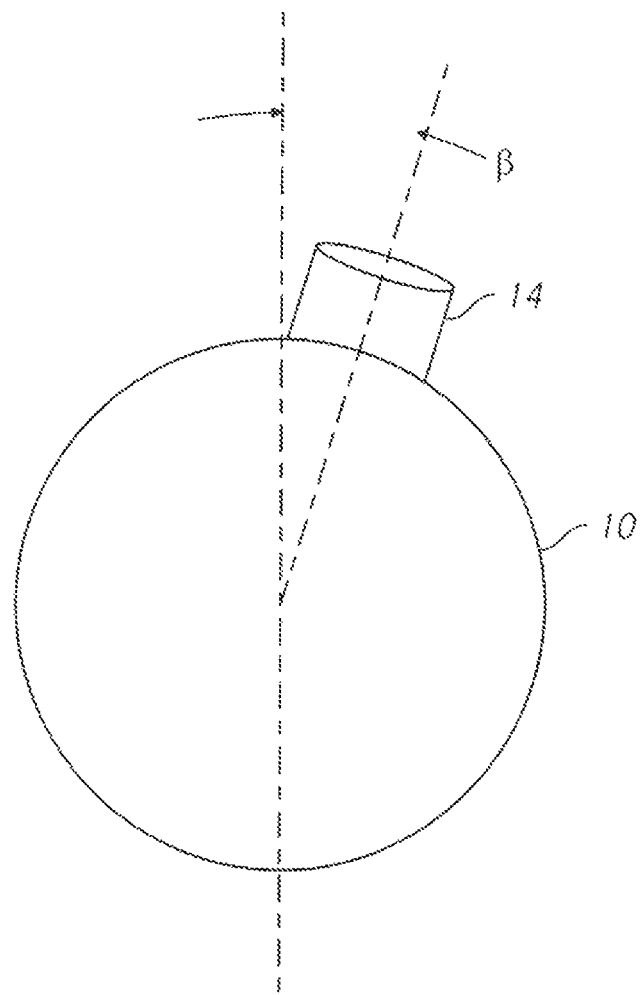
FIG. 4B is a sectional elevation view, showing the effect of slope (roll) on an underground storage tank.
Figure 5:
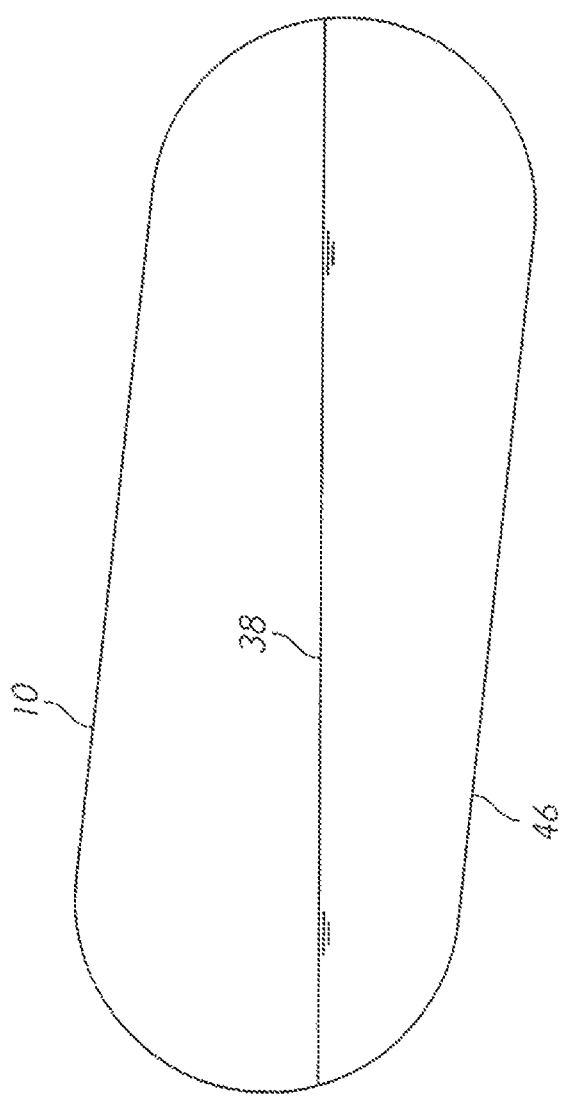
FIG. 5 is a sectional elevation view, showing the effect of uneven soil subsidence on an underground storage tank.
Figure 6:
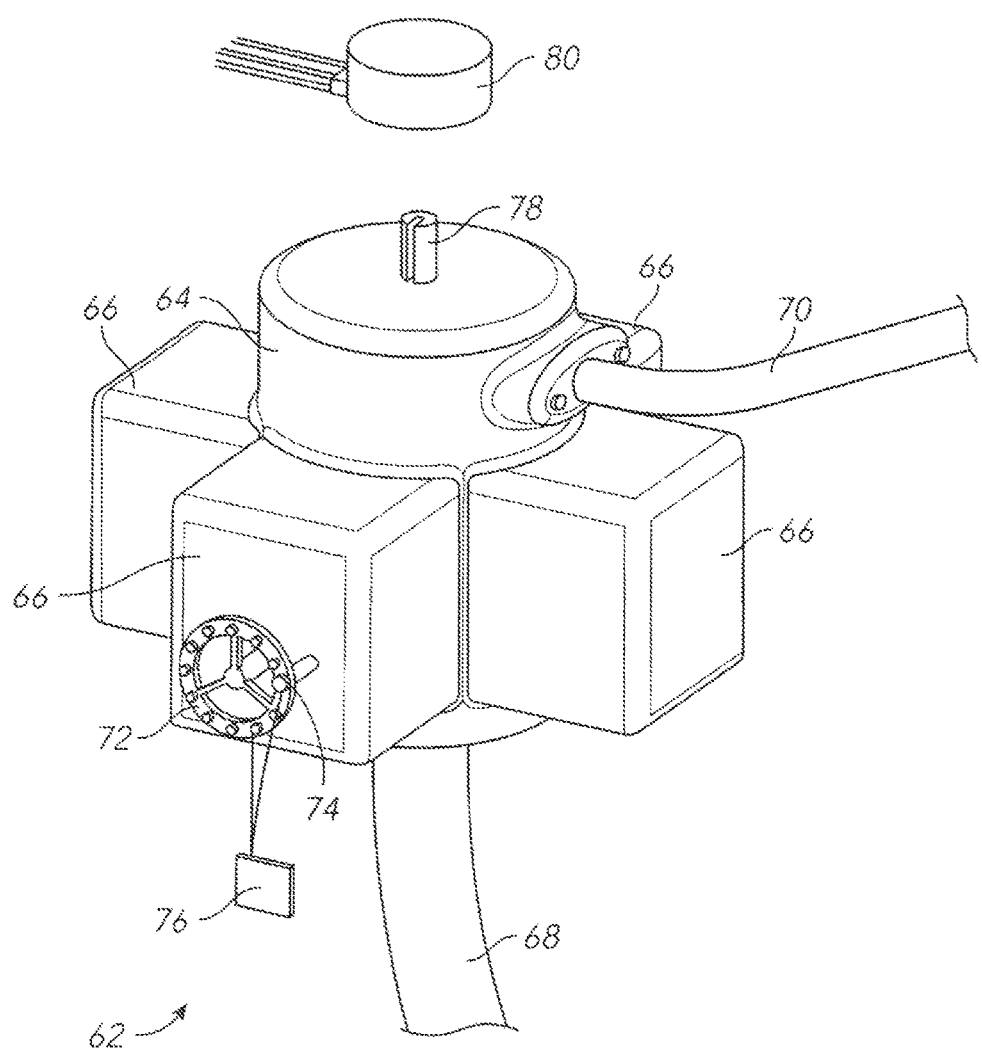
FIG. 6 is a perspective view, showing a prior art piston flow meter.

REFERENCE NUMERALS IN THE DRAWINGS 10 tank
12 fuel
14 fill access
16 fill pipe
18 slab
20 fill media
22 automatic tank gauge controller
24 ATG probe
26 probe head
28 pump
30 intake line
32 discharge line
34 vent
36 dispenser
38 surface
40 ullage
42 circular section
44 slumped section
46 bottom
48 flow meter
50 rotor
52 lobe
54 tip
56 inlet
58 outlet
60 sensor
62 piston flow meter
64 housing
66 cylinder cover
68 input pipe
70 output pipe
72 calibration wheel
74 lock pin
76 calibration seal
78 meter output shaft
80 rotary encoder
82 valve
84 user interface panel
86 nozzle receiver
88 nozzle feed line
90 inferential meter
92 electrical output
94 turbine meter
96 housing
98 turbine wheel
100 bearing assembly
102 pickoff coil
104 densitometer
106 electrical interface
108 fuel inventory processor
110 memory
112 temperature sensor
114 display
116 user interface devices
118 tank temperature sensor
120 fuel level float
122 water level float
124 temperature sensor
126 fuel/water interface

DETAILED DESCRIPTION

The present invention proposes to measure the density of a liquid being dispensed in real-time and use that information to monitor the accuracy of a volumetric flow meter. The specific embodiments disclosed pertain to the dispensing of fuels, through the invention may certainly have other applications.

A liquid densitometer is placed in a convenient location in the fuel storage and dispensing system. It measures the density of the fuel just prior to or just after the fuel passes through the regulating flow meter (typically a piston flow meter) so that the densitometer effectively measures the density of the fuel as it is being dispensed. There are several different types of densitometer and the invention is not limited to any particular type. However, one currently suitable densitometer uses the "tuning fork approach" and this particular type will be described for the reader's benefit.

In such a device a carefully-shaped vibrating element is excited while submerged in the liquid being measured. The exciting force is then removed and the vibration of the element is allowed to decay while it remains immersed in the liquid being measured. The decaying vibration is precisely measured by a transducer—such as a piezoelectric element. Variations in the decay function are then used to determine the density and viscosity of the liquid in which the vibrating element is immersed. Since viscosity adds a damping force, the decay function of the vibrating element is dependent on the density of the liquid in which the element is submerged.

The vibrating element in the densitometer is typically excited by a piezoelectric element, which may be the same piezoelectric element that is used to measure the decay function. The relationship of computed density to the decay function is somewhat dependent upon temperature and pressure. Thus, an accurate temperature sensor is often used in conjunction with the vibrating element. The temperature sensor may be part of the same instrument housing or it may be part of a separate housing.

Those skilled in the art will know that pressure variations can also affect the computation of density. However, a fairly significant change in pressure is generally needed to make a measurable difference (within a reasonable range). The pressure at the liquid surface level within the tank is always close to 1 bar. The pressure at the tank bottom may be higher—up to 1.5 bar. The pressure downstream of the pump may be much higher—often 3 to 8 bar. Even this amount of variation in pressure does not introduce a significant error in the coefficients. Thus, the accurate measurement of pressure is not really needed.

Further, it is possible by suitably placing the densitometer to effectively eliminate pressure-induced variation. For example, one can place the densitometer on the pressurized side of pump 28 in the system of FIG. 1. The densitometer then "sees" a near constant pressure (when the pump is energized) and the effect of pressure variation is effectively eliminated.

The reader wishing to know additional details regarding the nature and operation of liquid densitometers is referred to pending U.S. patent application Ser. No. 14/394,085. This application lists Eric Donzier as its inventor. It is published as U.S. Pub. No. 2015/0075279.

The instrumentation available to the present inventive system will now be described. Looking still at FIG. 1, ATG probe 24 provides precise liquid level measurements of the fuel residing in the tank (as well as the temperature of the fuel residing in the tank). Looking now at FIG. 8, the reader will recall that the fuel dispenser includes a piston flow meter 62. Rotary encoder 80 provides a pulsed output corresponding to the rotation of the output shaft within the piston flow meter. By counting the pulses, a separate control system can accurately determine the volumetric flow measured by the piston flow meter.

Figure 8:
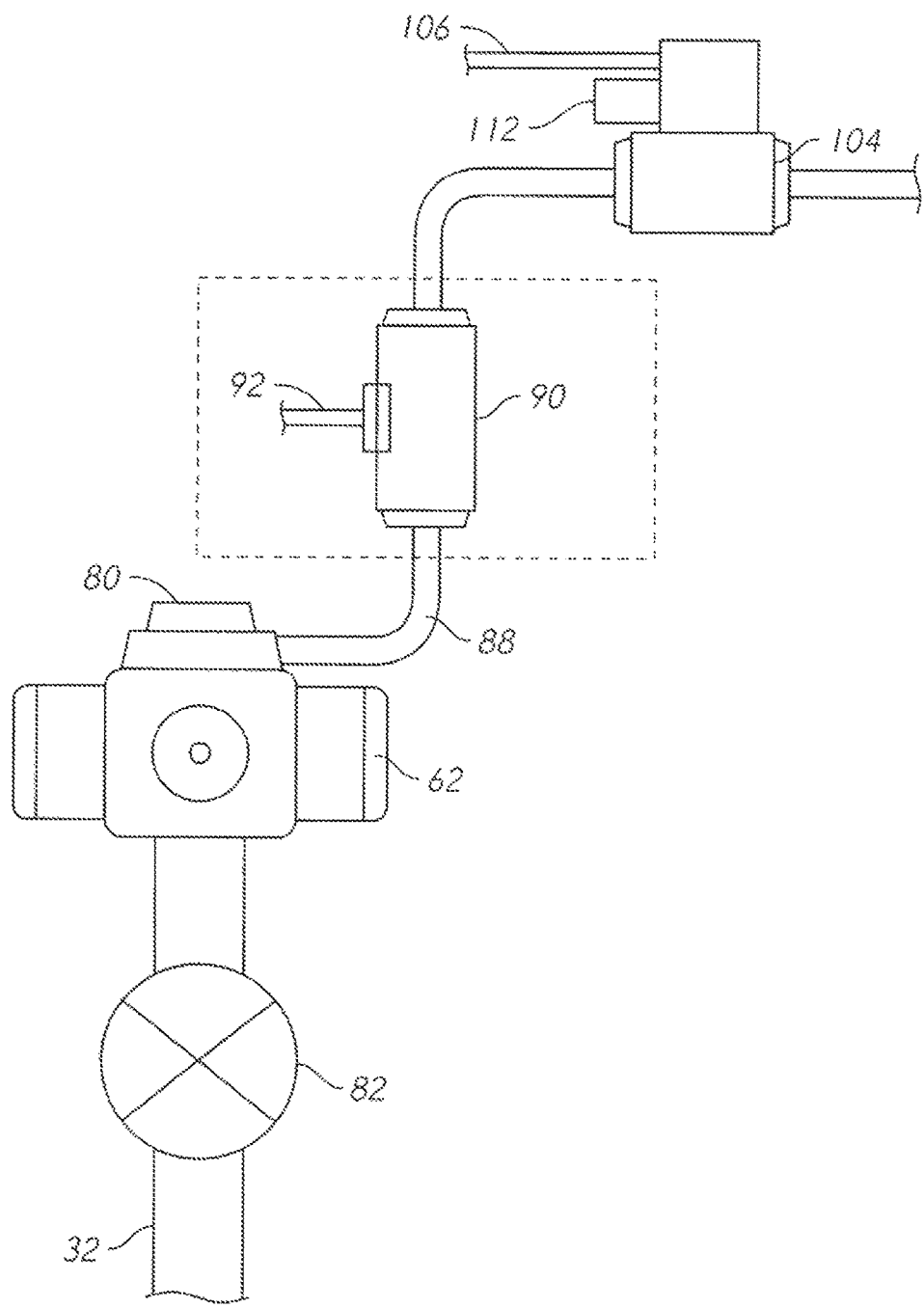
FIG. 8 is an elevation view, showing the addition of an inferential flow meter for use in the present invention.

Since one purpose of the liquid densitometer is to monitor the calibration of the piston flow meter, it is advantageous to place the densitometer as close to the flow meter as possible. In the embodiment of FIG. 8, an optional inferential flow meter 90 is shown inside the dashed lines. In many instances there will be no inferential flow meter and liquid densitometer 104 will be placed near the output of piston flow meter 62. The reader will recall that nozzle feed line 88 leads out of piston flow meter 62. This is the line that actually leads to the dispenser nozzle itself. If present, inferential meter 90 may be placed first in line. Densitometer 104 is preferably placed near the flow meter output. Electrical interface 106 provides power to the densitometer. It also carries information from the densitometer to a processor. The information may be a digital transmission or simply an analog value.

A fuel temperature sensor is preferably included in or near the densitometer. Alternatively, a separate temperature sensor may be used. In the example of FIG. 8, temperature sensor 112 is included in the same housing as densitometer 104. When fuel is being dispensed, densitometer 104 provides values for the density of the fuel. These values may be taken at fixed intervals if desired.

Figure 9:
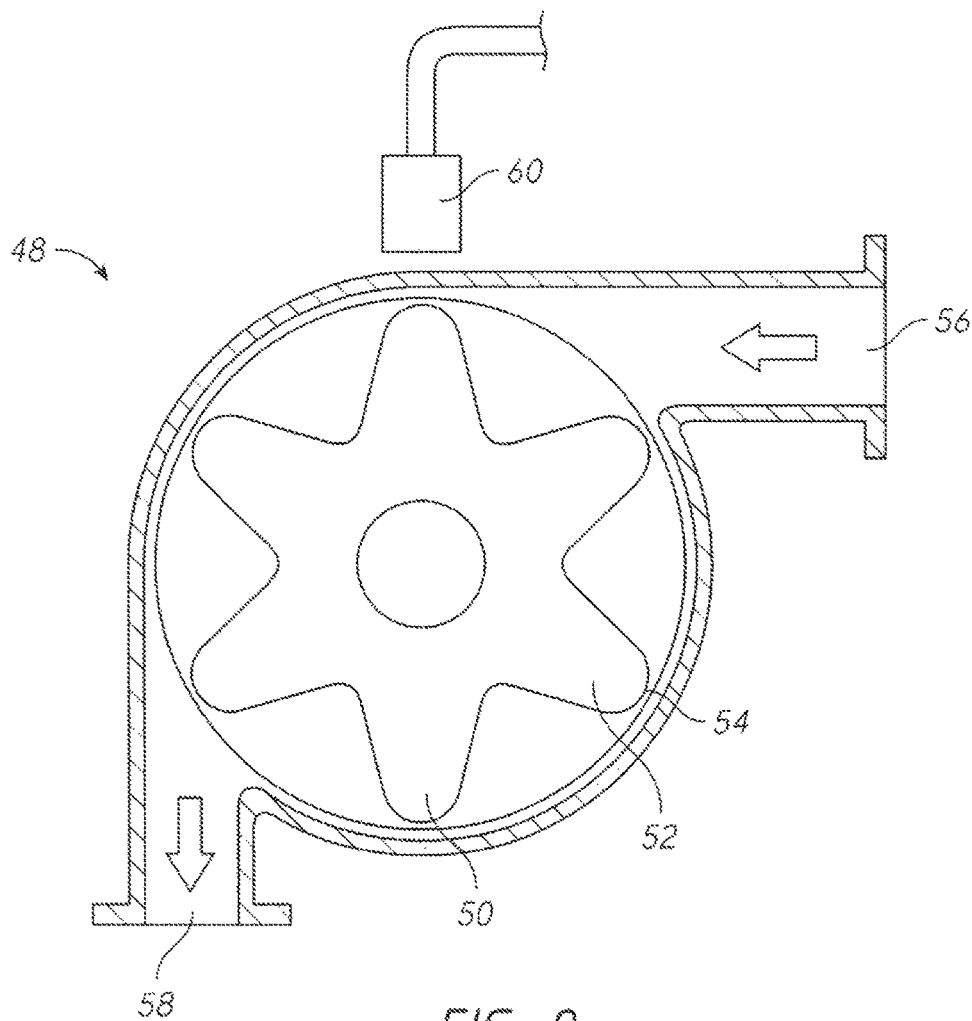
FIG. 9 is an elevation view, showing one type of inferential flow meter.
Figure 10:
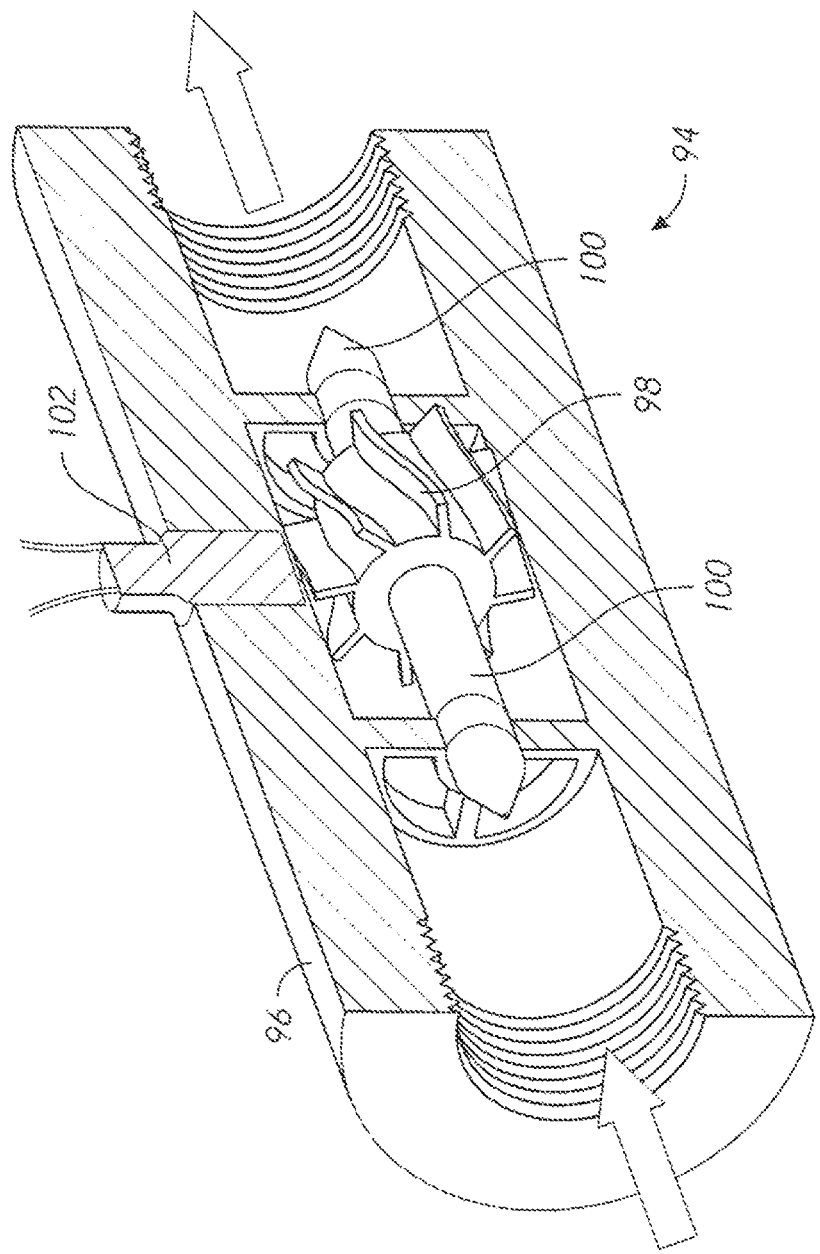
FIG. 10 is a sectional perspective view.

On the output side of the piston flow meter (nozzle feed line 88), a separate inferential flow meter 90 may also be added. This inferential flow meter has an electrical output 92. The term "inferential flow meter" is intended to encompass any device that accurately measures a volumetric flow and provides an electrical output from which the volume flowing through the device may be inferred. There are many different types of devices that could be used. FIGS. 9 and 10 present two such devices.

The inferential meter of FIG. 9 is sometimes referred to as a "gear meter." Fuel flows in through inlet 56 and outlet 58. Rotor 50 rotates within the housing. Multiple lobes 52 are provided. Tips 54 provide a close fit with the inside of the housing. It is not a positive displacement device in the strictest sense. However, the rotational speed of rotor 50 is highly related to the volumetric flow. This is particularly true for a range of flow rates in which the device is calibrated. Fuel dispensing occurs over a fairly narrow flow range so a gear meter can be quite accurate.

Sensor 60 is activated by the passing of each tip. As an example, rotor 50 may be made of a ferromagnetic material and sensor 60 may be a Hall effect sensor. The result is that an electrical pulse is produced each time a tip 54 passes sensor 60. The frequency of the pulse train then corresponds to a volumetric flow rate. An external processor monitors the frequency and stores this information to be used to determine the flow rate.

FIG. 10 shows another type of inferential meter—turbine meter 94. Fuel being dispensed flows axially through the device as indicated by the arrows. Turbine wheel 98 is suspended in the flow via rotary bearings 100 and at least one thrust bearing. The moving fluid spins the turbine wheel. Pickoff coil 102 senses the passing of each blade tip of the turbine wheel. Thus, flow is converted into a train of electrical pulses.

Although a turbine meter such as shown in FIG. 10 is not a positive displacement device, it can be very accurate. Such devices are calibrated for a range of flows and—within that range—the accuracy is very good. The fuel dispensing tends to remain within a defined range so a turbine meter provides a good result for this application. Further, the accuracy of a turbine meter does not tend to "drift" over time because there is no direct contact between the moving parts that actually make the measurements.

The present invention is able to achieve many goals that are useful to the liquid dispensing industry. Among these goals are:

(1) The determination of fuel density at the time the fuel is being dispensed;

(2) The verification of the accuracy (or detection of inaccuracy) of the mechanical flow meter over time (referring to the mechanical flow meter that is required for regulatory purposes);

(3) Detecting when the mechanical flow meter drifts outside a defined allowable tolerance;

(4) Recurring tank recalibration based on measured depth and the amount of fuel dispensed (automatically "restrapping the tank"); and (5) Enhancing the accuracy of statistical inventory reconciliation ("SIR")—referring in the fuel industry to the process of reconciling the amount of fuel dispensed against the amount loaded in the tank and the amount remaining in the tank.

An integrated process controller is preferably provided in the invention. A programmable logic controller might suffice in many installations. As another example, a data interface and controlling software could be added to a microcomputer already installed at a fuel-dispensing facility.

Figure 11:
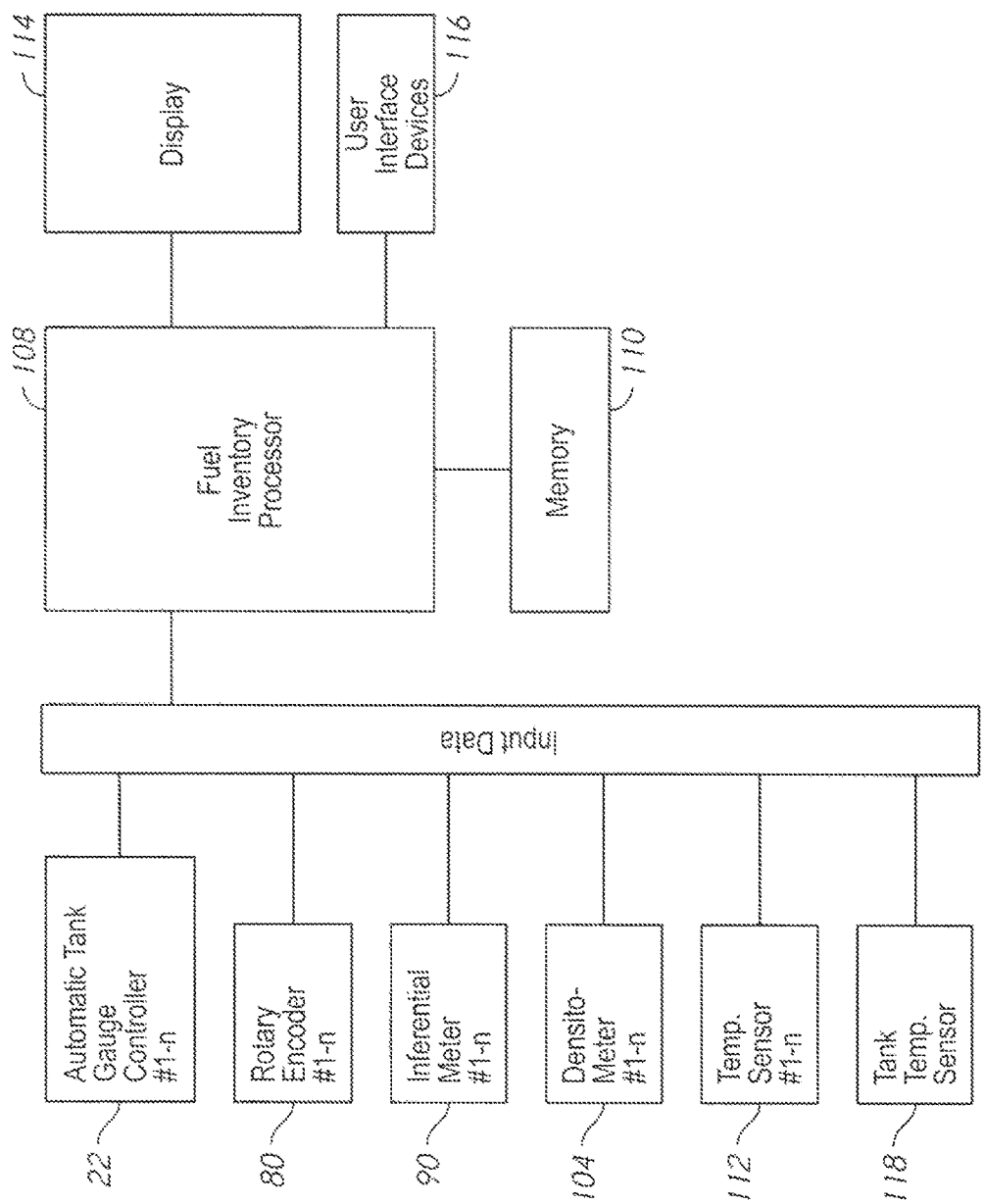
FIG. 11 is a schematic view, showing how the components of an exemplary inventive system interact.

FIG. 11 shows a block-diagram depiction of an exemplary process controller and its inputs and outputs. Fuel inventory processor 108 runs the controlling software. Associated memory 110 allows the processor to store and retrieve information as needed. Display 114 provides visual displays for a user to review. User interface devices 116 (keyboard, mouse, etc.) allow a user to interact with the software.

On the left side of the view the input data sources are shown. In this example, a single fuel inventory processor 108 collects data and performance calculations regarding multiple underground storage tanks. In this example there are four storage tanks (unleaded, unleaded mid-grade, unleaded-premium, and diesel). The measured level in each tank is furnished by an automatic tank gauge controller 22 associated with that tank. The ATG controller 22 may provide the depth value it actually determines or it may provide raw data for use by processor 108 (for instance, the depth value might be a depth in millimeters whereas the raw data might simply be a digital number in the range 0 to 2,047). A single ATG controller may in some instances handle multiple tanks. In other cases each individual tank will have its own stand-alone ATG controller.

Figure 7:
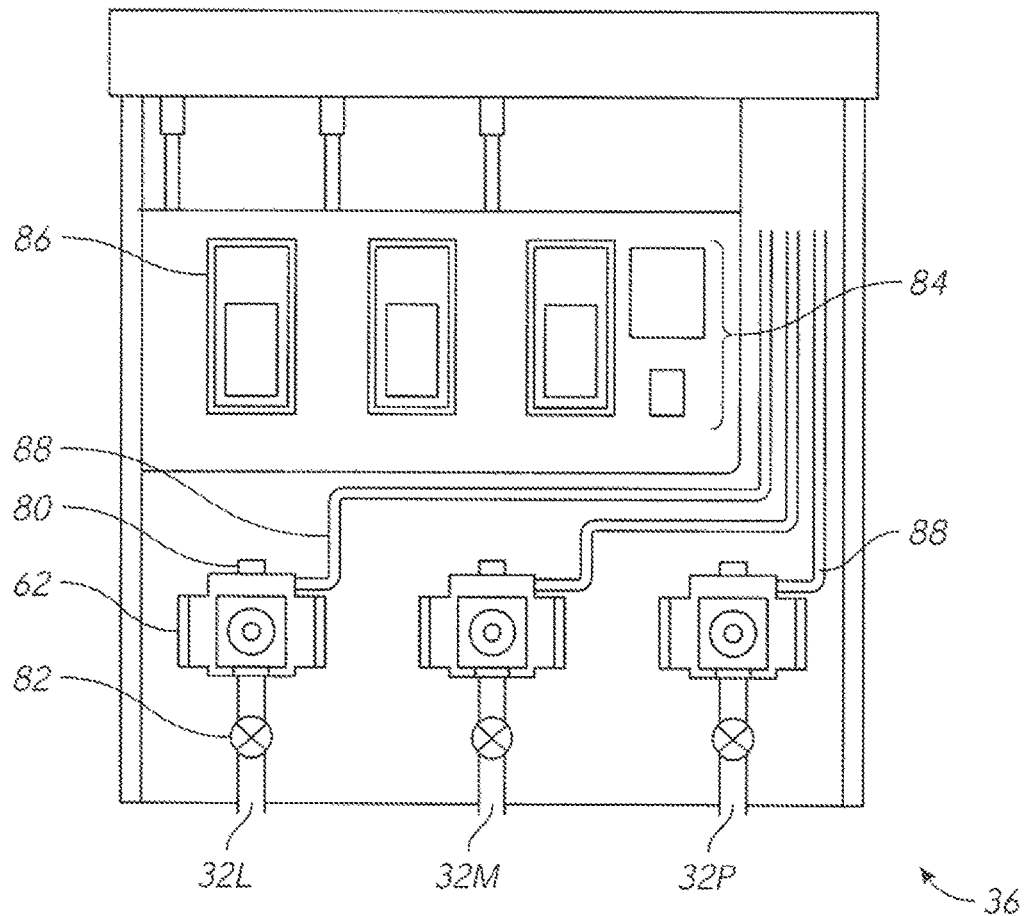
FIG. 7 is an elevation view, showing a prior art fuel dispenser.

Rotary encoders 80 provide data to the fuel inventory processor as well. The reader will recall that each piston flow meter is typically equipped with its own rotary encoder. Looking briefly at FIG. 7, the reader will also recall that each dispenser 36 may include three or more piston flow meters and therefore three or more rotary encoders. A typical dispensing station might have six gasoline dispensers with three rotary encoders each. It might also have two stand-alone diesel dispensers with two more rotary encoders. This would create a total of twenty rotary encoders 80 feeding onto the input data bus and ultimately to fuel inventory processor 108.

Of course, the connection to the rotary encoders may not be a direct one. The rotary encoders often feed into a separate system for displaying the fuel volume dispensed and receiving customer payment. Such a separate system might provide the interface to the fuel inventory processor. That interface could assume the form of a summary, such as: "Encoder #4/assigned-unleaded-mid-grade/14,421 pulses counted." Fuel inventory processor 108 would then need additional stored information to convert the pulse count into a volume of dispensed fuel measured by the piston pump to which Encoder #4 is attached.

Inferential flow meters 90 (if present) also feed data to the fuel inventory processor. There are different ways to arrange the inferential flow meters. In the example of FIG. 8, inferential meter 90 is installed in the output line from a single piston flow meter 62. In this scenario a meter 90 is needed for each fuel type, so if a dispenser dispenses three grades then three inferential flow meters 90 would be needed.

On the other hand, many dispensers feed the different type of fuels into a single dispenser nozzle. In that type of installation one could place a single inferential meter 90 on the line that feeds the single dispenser nozzle. Thus, there may be at least one inferential flow meter 90 for each dispenser and in many cases there will be multiple inferential flow meters in each dispenser. However, it is also possible to use a single inferential flow meter for each fuel tank. Returning to FIG. 1, it is possible to put a single inferential flow meter on the output side of pump 28. Then, no matter which dispenser is ultimately dispensing the fuel, the volume of fuel being pumped out of the tank can be measured. Although, depending on the length of the piping leading to the various dispensers and other characteristics, the use of a single inferential flow meter per tank may degrade the available accuracy.

Returning to FIG. 11—however many inferential flow meters 90 are used, they all feed output data to fuel inventory processor 108. The data may be "raw" (usually a series of voltage pulses). Alternatively, some types of flow meters include a small on-board processor that converts the readings to a digital output. Still others provide an output that is already converted to a measured volume. The fuel inventory processor can be configured to accommodate any of these types as well as others.

Multiple densitometers 104 also fed data to the fuel inventory processor. As for the inferential flow meters, the densitometers can be placed in different locations. These include: (1) a single densitometer in the pump discharge line for each tank, (2) a single densitometer in each dispenser (for those dispensers using a single nozzle), and (3) multiple densitometers in each dispenser (such as one for each fuel type).

Temperature sensors 112 also feed data to the fuel inventory processor. These may be mounted in multiple locations, as for the densitometers. It is preferable to mount them close to the nozzle and close to the densitometers. This location is shown in FIG. 8. Other locations are possible as well.

Figure 12:
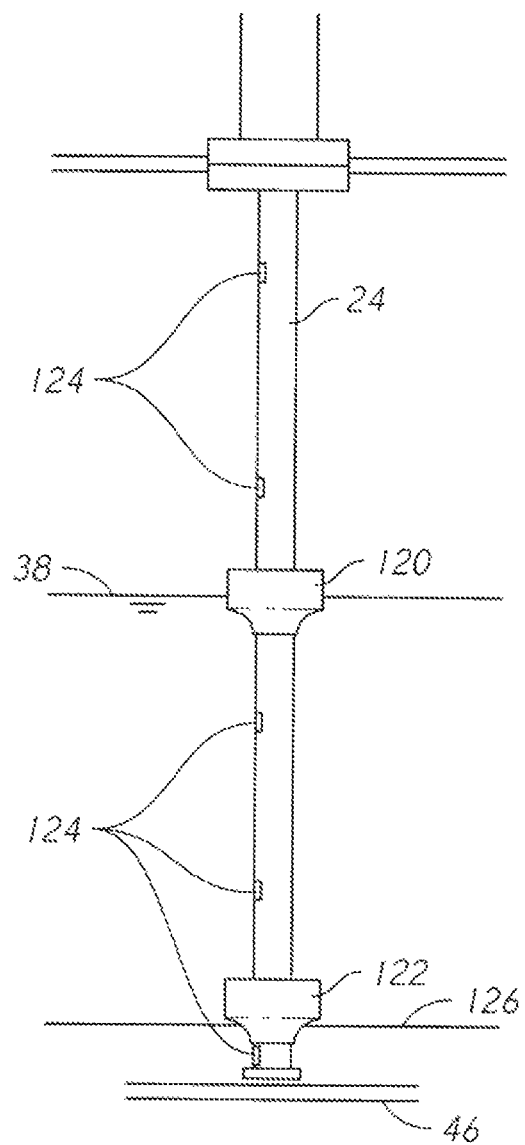
FIG. 12 is an elevation view, showing some of the features of an automatic tank gauge.

A desirable feature is the use of a temperature sensor in the tank itself. This is shown in FIG. 1, where tank temperature sensor 118 is mounted near the bottom of ATG probe 24. The more advanced version shown in FIG. 12 averages the temperature provided by all the sensors that are actually immersed in the fuel. Knowing the temperature of the fuel in the tank is helpful in reconciling depth variations caused by temperature change.

The reader should note that some of the sensors described may be omitted in some implementations. For example, temperature sensor 112 may be omitted for densitometers operating in a temperature range where the lack of temperature correction does not introduce significant error. The reader should also bear in mind that some densitometers have an internal temperature sensor and an internal temperature correction algorithm. This type of sensor just outputs a density value.

In the preferred embodiments, the inferential flow meter and the densitometer (and possibly associated temperature sensor) are located as close together as possible. This is done because of temperature variation of the fuel during pumping. On very hot days, the fuel temperature rises significantly between the tank and the dispenser nozzle. In extreme cases, the rise can be as much as 14° C. On very cold days, a substantial temperature drop may be experienced as well. In order to be a useful measurement, the density measurement should be made at or very near the volume measurement made by the inferential flow meter.

The operation of the inventive system will now be described using some examples. The reader should bear in mind that the examples provided are only a small sample of the many different ways the inventive system can be used.

EXAMPLE ONE

One approach is to monitor inventory in terms of fuel mass. The calculation and monitoring of mass would preferably be done internally, with the reporting being available in both volume and mass (since volume is customarily used in the industry). The example will pertain to inventory control of a single underground tank. The tank in question is a 38 cubic meter (approximately 10,000 U.S. gallon) gasoline tank configured to store "regular unleaded" gasoline. The tank is empty at the beginning of this example. A metered delivery is made by a tanker truck having a 34 cubic meter capacity and the entire capacity is emptied into the tank.

The "gross" delivery of 34 cubic meters (8,982 U.S. gallons) is made at an average temperature of 30° C. (86° F.). This delivery is corrected to "net" using a correction factor of 0.9811 for a net delivery of 33.3574 m$^3$ (8,812 U.S. gallons) The density of gasoline at net conditions (15° C.) is 730 kg/m$^3$ (45.98 bm/ft$^3$). Thus, the mass of fuel delivered is 24,351 kg (53,670 lbm). This amount is stored and logged in memory 110 associated with fuel inventory processor 108.

Looking at FIG. 1, the reader will recall that ATG probe 24 measures the depth of fuel within tank 10. The tank is delivered with a "strapping chart" correlating depth to volume contained (a "depth-to-volume relationship"). The tank in questions has a maximum depth of 3.0 meters and a length of 5.376 meters. After the fuel delivery, ATG probe 24 sends data regarding the position of surface 38 to automatic tank gauge controller 22. The measured depth is 2.684 meters (105.7 inches).

The strapping chart is most often a table having entries for measured depth and corresponding entries for the volume of fuel corresponding to the measured depth. The table in this example has many entries—separated by 5 mm increments. Linear interpolation is used to calculate values lying between the table entries. The strapping chart is used to look up the volume corresponding to the closest depth value in the table and linear interpolation is then used to find the volume corresponding to a measured depth of 2.684 meters (105.7 inches). Fuel inventory processor 108 performs these steps and determines the corresponding volume to be 33.3200 cubic meters (8,802 U.S. gallons). The actual volume delivered was measured at 34.0000 cubic meters (8,982 U.S. gallons), and since little time has passed since the delivery the fuel is essentially still at the temperature it had when it left the tanker and should still measure 34.0000 cubic meters. But 33.3200 cubic meters is seen in the chart. An error in the strapping chart is thereby observed. The strapping chart "says" the tank should contain 33.3200 cubic meters but in fact it is known that the tank contains 34.0000 cubic meters. This is a difference of 0.68 cubic meters (180 U.S. gallons). This is an error of 2% and is in the typical range of error for real-world installations.

The reader will recall that recurring tank recalibration based on measured depth and the amount of fuel dispensed (automatically "restrapping the tank") is one of the objectives of the invention. Fuel inventory processor 108 runs tank strapping error correction functions. These may assume many forms. Here is an example of an error correction function:

(1) The processor retrieves the value for the mass of fuel that is expected to be in the tank and the value for tank temperature sensor 118;

(2) The processor calculates the present volume of fuel in the tank based on the mass of fuel believed to be in the tank and the current temperature of the fuel;

(3) The processor retrieves the current depth reading for the fuel in the tank;

(4) The processor retrieves the current version of the tank strapping chart and determines the volume of fuel that the strapping chart says should be in the tank based on the depth reading (using the nearest depth value in the chart without interpolation);

(5) The processor averages the volume value retrieved from the strapping chart and the volume calculated in step (2); and (6) The processor stores the averaged value as the new value in the stored strapping chart as the proper volume associated with the nearest depth value in the chart to the depth value actually measured by the ATG probe.

This process corrects and updates the strapping chart over time, with averaging being used to smooth the variations. One could add interpolation to this process for increased accuracy, but provided that a table having small increments is used interpolation offers little increased accuracy.

The reader should bear in mind that some tanker deliveries are "unmetered." Payment in such a case is made on the basis of a change in volume in the tank before the delivery and after the delivery. The process is not quite that simple, however, as fuel will also be dispensed to paying customers while the tanker truck is unloading. For this reason, the inventive system can consider the calculated tank mass for a period of one hour before the tanker delivery to one hour after the tanker delivery. A substantial additional mass will be present at the close of this period and this additional mass may be considered to be the result of the tanker delivery.

EXAMPLE TWO

Of course, the temperature of the fuel in the underground tank does not remain constant over time. In the facts of EXAMPLE ONE the temperature of the fuel started at 30° C. (86° F.) but the temperature will gradually fall to the underground ambient temperature of 24° C. (75° F.). Those skilled in the art will know that this is a non-linear, asymptotic function. In the real world it is unusual for fuel to sit in a tank without some being continually dispensed. However, in this EXAMPLE TWO, it is assumed that no dispensing of the fuel occurs for one day and the fuel temperature by the end of that elapsed period is 24° C. (75° F.).

A significant volume change will occur. The 34.0000 cubic meters (8,982 U.S. gallons) of fuel pumped in will "shrink" to 33.7728 cubic meters (8,922 gallons—a reduction of 0.7%) even though no fuel has been dispensed. The ATG probe will also measure a corresponding reduction in depth. In ordinary systems a fuel leak might be suspected. However, in the inventive system, fuel inventory processor 108 monitors the tank temperature and calculates (or stores and looks up) the volume and depth changes expected with changes in temperature. The method that may be used is essentially the same as for the prior example:

(1) The processor retrieves the value for the mass of fuel that is expected to be in the tank (which is unchanged from the original state sine no dispensing has occurred) and the value for tank temperature sensor 118 (which may in fact be an average taken of several wetted sensors in the tank);

(2) The processor calculates the present volume of fuel in the tank based on the mass of fuel believed to be in the tank and the current temperature of the fuel;

(3) The processor retrieves the current depth reading for the fuel in the tank;

(4) The processor retrieves the current version of the tank strapping chart and determines the volume of fuel that the strapping chart says should be in the tank based on the depth reading (using the nearest depth value in the chart without interpolation);

(5) The processor averages the volume value retrieved from the strapping chart and the volume calculated in step (2); and (6) The processor stores the averaged value as the new value in the stored strapping chart as the proper volume associated with the nearest depth value in the chart to the depth value actually measured by the ATG probe.

Using this approach the fuel inventory processor "knows" that temperature-induced tank volume change does not demonstrate a leak and is instead expected. Relatively large errors may be encountered the first time the system is run (depending on how inaccurate the baseline tank strapping chart is) but these errors will be reduced over time until they are negligible.

The reader should note, however, that a disturbance to the tank configuration will introduce new errors. For example, if one end of the tank settles 3 cm over a two month period the existing strapping chart would ordinarily become inaccurate. But, since the inventive system is continually updating the strapping chart such errors do not grow and will in fact be corrected over time.

EXAMPLE THREE

EXAMPLE TWO provides a baseline for the reader's understanding but it is admittedly unrealistic. Fuel does not tend to sit in an underground tank. Rather, it is dispensed into vehicles immediately after it is delivered (and while it is being delivered). The mass in the tank is therefore not constant. It is increased when a tanker makes a delivery and it thereafter decreases until the next tanker delivery. Step (1) in both the prior examples requires the processor to retrieve the value for the mass of fuel that is expected to be in the tank. This value must be updated as fuel is dispensed.

Returning to FIG. 8, in this example piston flow meter 62, densitometer 104, and temperature sensor 112 are placed in the nozzle feed line 88 as shown. When a dispensing cycle commences, piston flow meter 62 accurately measures the volumetric flow of fuel. At the same time, densitometer 104 measures the density of the fuel. As explained previously, a temperature reading may be used internally by the densitometer to correct the reading for density or externally by fuel inventory processor 108 to correct the density. In either event, an accurate density for the fuel is obtained. Both a volume dispensed and a density value will be recorded for each dispensing operation.

This example covers the time period from 24 hours after the delivery of the fuel in EXAMPLE ONE until 48 hours after the delivery. During this period, the fuel inventory processor recorded 381 dispensing transactions involving the single tank of this example. A volume dispensed was measured for each individual transaction and a fuel density for each was measured as well. Using these two values, fuel inventory processor 108 determines a total mass of fuel dispensed. In this case the total mass of fuel dispensed is 17,387 kg, or 38,332 lbm (out of the original total of 24,351 kg or 53,685 lbm).

At defined periods throughout the 24 hour period in this example, fuel inventory processor 108 calculates the mass remaining in the tank and updates the strapping chart as for the prior examples, using essentially the same error correction function (with the addition of the mass reconciliation steps):

(1) The processor retrieves the value for the mass of fuel that was determined to be in the tank in the immediately preceding iteration:

(2) The processor calculates the mass of fuel dispensed since the prior iteration (using the information from the inferential flow meter and the densitometer);

(3) The processor calculates the present mass of fuel in the tank;

(4) The processor calculates the present volume of fuel in the tank based on the mass of fuel calculated and the current temperature of the fuel;

(5) The processor retrieves the current depth reading for the fuel in the tank;

(6) The processor retrieves the current version of the tank strapping chart and determines the volume of fuel that the strapping chart says should be in the tank based on the depth reading (using the nearest depth value in the chart without interpolation);

(7) The processor averages the volume value retrieved from the strapping chart and the volume calculated in step (2); and (8) The processor stores the averaged value as the new value in the stored strapping chart as the proper volume associated with the nearest depth value in the chart to the depth value actually measured by the ATG probe.

The defined periods may simply be fixed intervals of time. It is advantageous to perform the calculations when the pump for the tank in question is not running. One might also want to wait a defined "settling period" to get the most accurate surface level reading. Intervals of no dispensing are common—even for a busy facility. Any time there is a "quiet time" for a particular tank an inventory reconciliation could be automatically commenced.

Using this approach a repeated series of calculations and values are fed into the strapping chart as the liquid surface gradually descends. Much of the strapping chart will thereby be updated during a single 24 hour period. Values that have not been updated likely will be updated over a few days of dispensing. The uppermost part of the strapping chart will be updated when the tank is filled to the top. Preferably the tank is regularly filled nearly to the top so that accuracy is obtained for this portion of the depth-versus-volume correlation.

Individual entries in the strapping chart may not be updated for some time (assuming that the liquid level never "rests" upon those particular entries). It may therefore be helpful to provide smoothing algorithms for the tabular data. A smoothing algorithm can be run periodically. It applies a curve-fit to the data and creates new values for individual "outlier" points. If, for example, an individual point lies well outside a curve fit to the 10 nearest surrounding points, the individual point could be "adjusted" to lie on the curve.

From these examples, the reader can see how the proposed invention is able to meet the exemplary five objectives stated at the beginning of this detailed description. The following explains how the objectives can be met:

(1) The determination of fuel density at the time the fuel is being dispensed—The densitometer 104 actually measures the density of the fuel as it is being dispensed. This value is stored for use by fuel inventory processor 108 in determining the actual quantity dispensed.

(2) The verification of the accuracy (or detection of inaccuracy) of the mechanical flow meter over time (referring to the mechanical flow meter that is required for regulatory purposes)—In addition to making the computations of tanker fuel loaded, fuel dispensed, and fuel remaining in the tank, fuel inventory processor 108 also receives and stores the output from the rotary encoders 80 located on the piston flow meters 62. There are two methods that may then be used to check the accuracy of the piston flow meters. First, an individual piston flow meter can be compared to the volumes measured by an inferential flow meter 90 that is connected in series. If the difference in volume measured by the two devices exceeds a defined threshold then a warning trigger is set. The user interface associated with the fuel inventory processor then informs the user that a calibration check on the piston flow meter needs to be performed. Second, a comparison calculation of fuel remaining in the tank can be made on the basis of the inventive system versus just the piston flow meters. A significant delta in this total would also indicate the need for recalibration (though in the case of several piston flow meters it might not be possible to isolate which meter was the problem). The piston flow meter can only be recalibrated by the entity authorized by law. However, it is possible to extend the required calibration interval using the inventive system since an out-of-calibration meter can be detected.

(3) Detecting when the mechanical flow meter drifts outside a defined allowable tolerance—This is explained in the preceding section.

(4) Recurring tank recalibration based on measured depth and the amount of fuel dispensed (automatically "restrapping the tank")—The inventive system continually updates the strapping chart. Errors introduced by tank sag, etc. can be eliminated over time.

(5) Enhancing the accuracy of statistic inventory reconciliation ("SIR")—Leak detection is a significant problem with the underground storage of fuel. By creating and maintaining an accurate strapping chart, the inventive system is able to detect a leak by noting a liquid level that is lower than it should be. If such a trend is monitored over a suitable time period then a leak may be assumed to exist.

The following additional components and features may be added in some embodiments of the invention:

(1) The inclusion of multiple temperature sensors at various points throughout the tank to improve the accuracy of the computed volume of fuel in the tank;

(2) The careful measurement of a "retained volume" in the distribution from the tank to the nozzle, which remains in place from the time the pump is shut off until the next dispensing cycle commences;

(3) The inclusion of one or more temperature sensors to measure the temperature of the retained volume and thereby improve the determination of a mass for this volume;

(4) The inclusion of flow-stabilizing devices for improving the accuracy of the densitometer; and (5) Embodiments omitting the inferential flow meter and just using the mandated piston flow meter. In these versions the densitometer would still allow tank mass calculations and strapping chart corrections over time. An error detection algorithm could then be run to determine if a creeping discrepancy represents an out-of-calibration piston flow meter.

Returning again to FIG. 8, the reader will recall that the preferred embodiments omit inferential meter 90 and only employ piston flow meter 62 for measuring the volume of dispensed fuel. In this case the only "check" on the continued accuracy of the piston flow meter is the reconciliation performed by the present system in creating a continually-updated relationship between the measured depth of the tank and the mass of fuel in the tank (which may be stated as a volume). This "check" is an important feature of the present invention and warrants further explanation.

A basic explanation of the operating principle could be stated as follows: (1) The system tracks the mass of fuel that is believed to be in the tank (including tracking inputs and outputs) and the system converts this mass to a volume believed to be in the tank using the temperature sensor(s) in the tank; (2) The system monitors the depth of the fuel in the tank using an accurate depth sensor; (3) The system builds an accurate depth-to-volume relationship (from measured depth and calculated volume) which precisely relates measured depth to the volume contained in the tank; (4) The system monitors the stability of the depth-to-volume relationship over time (It should be quite stable); (5) in the event of the depth-to-volume relationship beginning to drift, the system creates some kind of alert so that the operator can take action (such as recalibrating the piston flow meter).

Creation of the depth-to-volume relationship: An initial depth-to-volume relationship is almost always provided by a manufacturer for a new tank. As explained previously, this is often a simple "strapping chart" where a left-hand column states measured depth and a right-hand column states corresponding volume. It is also possible to state the relationship as a mathematical expression, such as the case of a simple horizontal cylinder:

$$v = r^2 \sqrt{1-y^2} y + \cos^{-1}(-y), \text{ where depth} = |-r-y|$$

A mathematical expression will be much more complex for most tank geometries. For this reason, curve-fitting techniques may be used instead. A value for depth will be measured by the system and a value for volume will be calculated. A suitable curve may then be fitted through the measured points. One or more splines may be used to curve-fit the data. A higher order spline (third order or higher) is preferably used to increase accuracy. The span of the data may be subdivided with different splines used to cover different portions of the data.

Of course, a simple table may also be created for the depth-to-volume relationship. Data storage capacity no longer presents a big problem. One could therefore create a table that includes an entry for every possible depth gauge reading. If, for example, the finest resolution of the depth gauge is a 1 mm increment, one could create a table in 1 mm increments. Some of the entries in such a table might not ever be populated, but in that case interpolation using adjacent entries could fill in the missing data.

Initial calibration of the depth-to-volume relationship: As stated, most tanks are delivered with a strapping chart and this can be used for the initial depth-to-volume relationship. The piston flow meter used to measure output is preferably calibrated at the outset so its accuracy is confirmed. Input measurements of volume (from a tanker drop) are also preferably well calibrated. When the inventive system begins running, the depth-to-volume relationship will be expected to change significantly since initial strapping charts nearly always contain errors. However, after the initial period, the depth-to-volume relationship should stabilize and remain stable for a long time.

Monitoring for instability: The calculation of mass in the tank depends largely on knowing the volume and density of the fuel dispensed from the tank. The density value is determined by a densitometer. The densitometer does not tend to "drift." Rather, it should work consistently up to the point of failure. The piston flow meter—on the other hand—will at some point drift out of calibration. An erroneous reading from the piston flow meter will show up as a change in the depth-to-volume relationship.

An example will illustrate this point. Assume that the piston flow meter drifts out of calibration and is now delivering a greater volume of fuel than is "reported" by counting the pulses of its rotary encoder. The result is that a greater mass of fuel is leaving the tank than is being accounted for by the inventive system. The actual mass in the tank then drops lower and lower in comparison to the calculated mass and the same will be true for the calculated volume.

Assume under the previously stable depth-to-volume relationship the system calculated a volume in the tank of 19.0 cubic meters (5,019 U.S. gallons) and this corresponded to a depth of 1,500 millimeters (59.05 inches). However, when the inventive system now calculates the volume of 19.0 cubic meters the actual measured depth is only 1,425 millimeters (56.10 inches). Further, the error trend is increasing over time so that one week later a calculated volume of 19.0 cubic meters corresponds to a measured depth of 1,410 millimeters (55.51 inches). At this point it is reasonable to assume that the piston flow meter has gone out of calibration.

Some changes in the depth-to-volume relationship will be seen regularly, but it should appear random. For example, the volume and temperature measurements for tanker drops are often not as precise as for dispensing operations. Thus, some tanker drops may be over-stated and others may be under-stated. These errors may cause the depth-to-volume relationship to shift but they should not cause it to steadily creep in one direction.

Defined initial period: The initial calibration of the depth-to-volume relationship may be done over a defined time period (such as 30 days). One may also allow the system to create the defined initial period automatically by monitoring the change in the depth-to-volume relationship and declaring it stable when the change drops below a defined stabilization threshold. Once the defined initial period is over, the system expects the depth-to-volume relationship to remain stable. The system then monitors to see if the depth-to-volume relationship exceeds a defined drift threshold. If this threshold is exceeded, the system provides an alert indicating that some form of recalibration may be needed. For instance, a defined drift threshold could be the presence of a depth disparity exceeding 10 mm that persists for a period of 3 days.

The inventive system preferably includes user interface features such as a display screen that is linked to the processor used to run the inventive software. In the event of the drift threshold being exceeded the system could cause a "calibration alert" to appear on a display screen. The display screen could even be presented on a tablet or smartphone that is linked to the processor by any suitable communication network.

The foregoing description of the preferred embodiments of the disclosed system has been presented to illustrate the principles of the disclosed system and not to limit the disclosed system to the particular embodiments illustrated. It is intended that the scope of the disclosed system be defined by all of the embodiments encompassed within the following claims and their equivalents, rather than by any particular example given.

Having described our invention, we claim:

1. A method for monitoring accuracy of a calibrated flow meter configured to measure a flow by volume of a liquid being dispensed from a storage tank and for correcting a depth-to-volume relationship for a storage tank configured to store a liquid, said storage tank having a depth sensor for measuring a depth of said liquid, a fill access for adding said liquid, an attached dispenser for dispensing said liquid, and a calibrated flow meter configured to measure a flow by volume of said liquid as said liquid is being dispensed, comprising:
   a. providing a processor running software, said processor including an associated memory;
   b. providing a user display configured to display information from said processor;
   c. storing an initial depth-to-volume relationship in said memory, said initial depth-to-volume relationship relating a volume of said liquid in said tank to a depth measured by said depth sensor;
   d. at a first time, said processor storing an initial value for a mass of liquid in said tank;
   e. providing a densitometer configured to measure a density of said liquid as said liquid is being dispensed;
   f. providing a tank temperature sensor for measuring a temperature of said liquid in said tank;
   g. at a second time, said processor determining a calculated volume of said liquid in said tank by
      i. calculating a mass of liquid dispensed from said tank since said first time using said flow by volume measurements from said calibrated flow meter and said density measurements from said liquid densitometer, wherein mass is calculated as volume measured by said calibrated flow meter times density measured by said densitometer,
      ii. calculating a mass of liquid added to said tank since said first time using volume delivered measurements through said fill access and corresponding temperature-as-delivered measurements, wherein said temperature-as-delivered measurements are used to determine density and mass is calculated as density times volume,
      iii. calculating a revised value for said mass of liquid in said tank by adding said mass of liquid added to said tank and subtracting said mass of liquid dispensed from said initial value for said mass of liquid,
      iv. calculating a revised volume of said liquid in said tank using said revised value for said mass of said liquid in said tank and a value for said tank temperature sensor, wherein said value for said tank temperature sensor is used to determine density and volume is calculated as mass divided by density,
   h. retrieving a current liquid depth value from said depth sensor;
   i. creating a revised depth-to-volume relationship using said current liquid depth value and said calculated revised volume, whereby said depth-to-volume relationship is expanded over multiple iterations to encompass multiple depths and multiple calculated volumes;
   j. said processor monitoring said depth-to-volume relationship for a defined initial period following an initial calibration of said calibrated flow meter;
   k. defining a baseline depth-to-volume relationship following an end of said initial period and storing said baseline depth-to-volume relationship in said memory;
   l. providing a defined drift threshold representing the maximum deviation for a current liquid depth value for a particular calculated tank volume compared to a corresponding liquid depth value for said calculated tank volume in said baseline depth-to-volume relationship;
   m. said processor monitoring for an exceedance of said defined drift threshold; and
   n. upon detection of said exceedance, said processor sending a message causing the presence of said exceedance to be displayed on said display, thereby indicating a need to recalibrate said calibrated flow meter.

2. The method for monitoring accuracy of a calibrated flow meter and correcting a depth-to-volume relationship for a storage tank as recited in claim 1, wherein said depth-to-volume relationship is a table storing individual depth values and corresponding individual volume values.

3. The method for monitoring accuracy of a calibrated flow meter and correcting a depth-to-volume relationship for a storage tank as recited in claim 2, wherein interpolation is used when a liquid depth value does not correspond exactly to a value in said table.

4. The method for monitoring accuracy of a calibrated flow meter and correcting a depth-to-volume relationship for a storage tank as recited in claim 1, wherein said depth-to-volume relationship is a mathematical function relating volume to measured depth.

5. The method for monitoring accuracy of a calibrated flow meter and correcting a depth-to-volume relationship for a storage tank as recited in claim 4, wherein said mathematical function is a spline.

6. The method for monitoring accuracy of a calibrated flow meter and correcting a depth-to-volume relationship for a storage tank as recited in claim 5, wherein said spline is a higher-order spline.

7. The method for monitoring accuracy of a flow meter and correcting a depth-to-volume relationship for a storage tank as recited in claim 1, wherein said processor determines said defined initial period by monitoring for changes in said depth-to-volume relationship and determining that said defined initial period has ended when changes in said depth-to-volume relationship fall below a defined stabilization threshold.

8. A method for monitoring accuracy of a calibrated flow meter configured to measure a flow by volume of liquid being dispensed from a storage tank and for correcting a depth-to-volume relationship for a storage tank configured to store a liquid, said storage tank having a depth sensor for measuring a depth of said liquid, a fill access for adding said liquid, an attached dispenser for dispensing said liquid, and a calibrated flow meter configured to measure a flow by volume of said liquid as said liquid is being dispensed, comprising:
- a. providing a processor running software, said processor including an associated memory and an associated display;
- b. storing an initial depth-to-volume relationship in said memory, said initial depth-to-volume relationship relating a volume of said liquid in said tank to a depth measured by said depth sensor;
- c. providing a densitometer configured to measure a density of said liquid as said liquid is being dispensed;
- d. providing a tank temperature sensor for measuring a temperature of said liquid in said tank;
- e. providing an initial calculated volume and calculated mass for said tank at a first time;
- f. over a defined initial period following said first time, periodically determining a calculated volume for said tank and associating a depth measured by said depth sensor with said calculated volume in order to create a baseline depth-to-volume relationship, by
  - i. calculating a mass of liquid dispensed from said tank since said first time using said flow by volume measurements from said calibrated flow meter and said density measurements from said liquid densitometer, wherein mass is calculated as volume measured by said calibrated flow meter times density measured by said densitometer,
  - ii. calculating mass of liquid added to said tank since said first time using volume delivered measurements through said fill access and corresponding temperature-as-delivered measurements, wherein said temperature-as-delivered measurements are used to determine density and mass is calculated as density times volume,
  - iii. calculating a revised value for said mass of liquid in said tank by adding said mass of liquid added to said tank and subtracting said mass of liquid dispensed from a previously calculated value for said mass of liquid,
  - iv. calculating a revised calculated volume of said liquid in said tank using said revised value for said mass of said liquid in said tank and a value for said tank temperature sensor, wherein said value for said tank temperature sensor is used to determine density and volume is calculated as mass divided by density,
  - v. retrieving a current liquid depth value from said depth sensor;
  - vi. wherein said baseline depth-to-volume relationship is expanded over multiple iterations to encompass multiple depth values and multiple calculated volumes:
- g. at the conclusion of said defined initial period, storing said baseline depth-to-volume relationship in memory;
- h. providing a defined drift threshold representing the maximum deviation for a current liquid depth value for a particular calculated tank volume compared to a corresponding liquid depth value for said calculated tank volume in said baseline depth-to-volume relationship;
- i. said processor monitoring for an exceedance of said defined drift threshold; and
- j. upon detection of said exceedance, said processor sending a message causing the presence of said exceedance to be displayed on said display, thereby indicating a need to recalibrate said calibrated flow meter.

9. The method for monitoring accuracy of a calibrated flow meter and correcting a depth-to-volume relationship for a storage tank as recited in claim 8, wherein said depth-to-volume relationship is a table storing individual depth values and corresponding individual volume values.

10. The method for monitoring accuracy of a calibrated flow meter and correcting a depth-to-volume relationship for a storage tank as recited in claim 9, wherein interpolation is used when a liquid depth value does not correspond exactly to a value in said table.

11. The method for monitoring accuracy of a flow meter and correcting a depth-to-volume relationship for a storage tank as recited in claim 8, wherein said depth-to-volume relationship is a mathematical function relating volume to measured depth.

12. The method for monitoring accuracy of a flow meter and correcting a depth-to-volume relationship for a storage tank as recited in claim 11, wherein said mathematical function is a spline.

13. The method for monitoring accuracy of a flow meter and correcting a depth-to-volume relationship for a storage tank as recited in claim 12, wherein said spline is a higher-order spline.

* * * * *